United States Patent
Bell

(10) Patent No.: US 6,872,408 B2
(45) Date of Patent: Mar. 29, 2005

(54) METHOD OF TREATING BIPOLAR DISORDERS USING DEUTERIUM-SUBSTITUTED CARBONATE

(76) Inventor: Rupert C. Bell, 1312 Oakland Dr., Room 109-Holder Building, Kalamazoo, MI (US) 49008

( * ) Notice: Subject to any disclaimer, the term of this patent is extended or adjusted under 35 U.S.C. 154(b) by 48 days.

(21) Appl. No.: 10/236,492

(22) Filed: Sep. 6, 2002

(65) Prior Publication Data

US 2003/0124201 A1 Jul. 3, 2003

Related U.S. Application Data

(60) Provisional application No. 60/318,027, filed on Sep. 7, 2001.

(51) Int. Cl.$^7$ .......................... A61K 33/00; A61P 25/18; A61P 25/24
(52) U.S. Cl. ....................... 424/715; 424/600; 424/686; 424/687; 424/716; 424/717; 514/899
(58) Field of Search .................... 424/600, 715–717, 424/686, 687; 514/899

(56) References Cited

U.S. PATENT DOCUMENTS

| | | |
|---|---|---|
| 4,473,585 A | 9/1984 | Abrahamsson et al. |
| 5,223,269 A | 6/1993 | Liepins |
| 5,846,514 A | 12/1998 | Foster et al. |
| 5,858,375 A | 1/1999 | Furminger et al. |
| 5,895,660 A | 4/1999 | Hoffmann et al. |

OTHER PUBLICATIONS

Ikeda, M. et al. Hydrogen–deuterium exchange effects on beta–endorphin release from AtT20 murine pituitary tumor cells. Biophysical Journal [online], [retrieved on Nov. 10, 2004]. Retrieved from the Internet <URL: http://biophys-j.org >.*

Purdue researchers discover basis for biological clock [onnline], [retrieved on Nov. 11, 2004]. Retrieved from the Internet <URL: http://www.brightsurf.com/news/jan_03/EDU_news_010803_d.html >.*

Chemical Abstracts, accession No. 126:246824; abstracting WO 97/09991 (1997).*

Martindale The Extra Pharmacopoeia, The Pharmaceutical Press, London, 1993, 30$^{th}$ ed., p. 257, entry for lithium carbonate on columns 2 and 3.*

Medline abstract, accession No. 89117301 (1999).*

DRUGU abstract, accession No. 1989–48938 (1989).*

EMBASE abstrract, accession No. 1999373472 (1999).*

Hayes and Palmer, Int. J. Chromobiol. 4: 63–69 (1976).

Douse and Palmer, Biol. Bull 143: 513–524 (1972).

Hayes and Plamer, Experientia, 4: 469–470 (1976).

* cited by examiner

*Primary Examiner*—John Pak
(74) *Attorney, Agent, or Firm*—Ian C. McLeod

(57) ABSTRACT

The present invention provides a method for treating psychiatric disorders such as mania or depression in a patients, in particular, patients with a bipolar disorder, by providing substantially isotopically pure heavy water substantially free of protons, isotopically pure hydrogen-containing water substantially free of deuterium, isotopically pure carbonate compounds substantially free of deuterium, isotopically pure carbonate compounds substantially free of protons, isotopically pure phosphate compounds substantially free of deuterium, isotopically pure phosphate compounds substantially free of protons, or mixtures thereof to the patient. In particular, the present invention provides a method for treating manic symptoms in a patient and mania or depression in patients with a bipolar disorder.

8 Claims, No Drawings

METHOD OF TREATING BIPOLAR DISORDERS USING DEUTERIUM-SUBSTITUTED CARBONATE

CROSS-REFERENCE TO RELATED APPLICATION

This application claims priority to Provisional Application Ser. No. 60/318,027, filed Sep. 7, 2001.

STATEMENT REGARDING FEDERALLY SPONSORED RESEARCH OR DEVELOPMENT

None.

BACKGROUND OF THE INVENTION (1) Field of the Invention

The present invention relates to a method for treating psychiatric disorders such as mania or depression in patients, in particular, patients with a bipolar disorder, by providing substantially isotopically pure inorganic compounds such as heavy water substantially free of protons, isotopically pure hydrogen-containing water substantially free of deuterium, isotopically pure carbonate compounds substantially free of deuterium, isotopically pure carbonate compounds substantially free of protons, isotopically pure phosphate compounds substantially free of deuterium, isotopically pure phosphate compounds substantially free of protons, or mixtures thereof to the patient. In particular, the present invention relates to a method for treating manic symptoms in a patient and mania or depression in patients with a bipolar disorder.

(2) Description of Related Art

Deuterium oxide, otherwise known as heavy water, has been shown to have a chronomutagenic effect on the period and entrainment of the light-dark (LD) cycle of mice (Hayes and Palmer, Int. J. Chromobiol 4:63–69 (1976); Douse and Palmer, Biol. Bull 143: 513–524 (1972)). In particular, it has been shown that deuterium oxide suppressed the spontaneous locomotor activity of the mouse (Hayes and Palmer, Experientia, 4: 469–470 (1976)). Other references of general interest are Rütger Wever, In: *The Circadian System of Man: Results of Experiments Under Temporal Isolation.* Springer Verlag, New York, N.Y. (1979); and, Mohammud & Sharon Shaffi, *In Phototherapy, Biological Rhythms, Mood Disorders, and the Pineal Gland*, American Psychiatric Press (1990). These cycles are also related to the manic depressive state in humans.

Lithium compounds are used for the treatment of manic depressive disorders; however, the lithium compounds are very dosage sensitive and can be toxic to the patient at high dosages. Thus, it would be desirable to provide compounds for the treatment of these psychiatric disorders, which are less dosage sensitive and less toxic than lithium-based compounds.

Deuterated compounds and compositions for use in pharmaceutical applications has been the object several patents. These patents have shown that particular deuterated compounds or compositions have enhanced stability or enhanced efficacy at lower dosage levels than their protonated analogs.

U.S. Pat. No. 4,473,585 to Abrahamsson et al. discloses deuterated acids, in particular perdeuterated N-hendecanoic acid or 2,2-dideutero-N-hendecanoic acid, and their use for protecting an object against attack by destructive fungi. The patent indicates that short chain compounds (citric acid) may have an undesired affect on humans.

U.S. Pat. No. 5,223,269 to Liepins discloses methods and deuterium containing compositions for treating hypertension. In particular, the compositions that are disclosed contain deuterium oxide, deuterated foods, or deuterated antihypertensive drugs.

U.S. Pat. No. 5,846,514 to Foster et al. discloses a method for enhancing drug efficiency and duration of action by using drugs wherein one or more hydrogen atoms of the drug are deuterated. In particular, the method produces deuterated compounds such as nifedipine, a drug for treatment of hypertension, and penicillins.

U.S. Pat. No. 5,858,375 to Furminger et al. discloses pharmaceutical compositions that consist of the drug in deuterium oxide wherein the deuterium oxide enhances the stability of the composition. In particular, the compositions relate to virus vaccines in a stabilizer consisting of deuterium oxide and other stabilizers.

U.S. Pat. No. 5,895,660 to Hoffmann et al. discloses a method for enhancing the adsorption of drugs in transdermal application wherein a deuterated analogue of the drug is applied the skin.

However, the prior art deuterated compounds have not been used to treat mental disorders such as mania or depression in patients with bipolar disorders.

SUMMARY OF THE INVENTION

The present invention provides a method for treating psychiatric disorders such as mania or depression in patients, in particular, patients with a bipolar disorder, by providing substantially isotopically pure heavy water substantially free of protons, isotopically pure hydrogen-containing water substantially free of deuterium, isotopically pure carbonate compounds substantially free of deuterium, isotopically pure carbonate compounds substantially free of protons, isotopically pure phosphate compounds substantially free of deuterium, isotopically pure phosphate compounds substantially free of protons, or mixtures thereof to the patient. The aforementioned compounds can be administered orally, intranasally, intravenously, or by inoculation. The preferred method is oral administration.

Therefore, the present invention provides a method of treating a depressive or manic symptom in a human patient which comprises administering isotopically pure heavy water substantially free of protons, isotopically pure hydrogen-containing water substantially free of deuterium, isotopically pure carbonate compounds substantially free of deuterium, isotopically pure carbonate compounds substantially free of protons, isotopically pure phosphate compounds substantially free of deuterium, isotopically pure phosphate compounds substantially free of protons, or mixtures thereof to the patient in an amount which reduces the manic (or depressive) symptoms of the patient.

Further, the present invention provides a method for effecting a mental change in a human which comprises administering an effective amount of isotopically pure heavy water substantially free of protons, isotopically pure hydrogen-containing water substantially free of deuterium, isotopically pure carbonate compounds substantially free of deuterium, isotopically pure carbonate compounds substantially free of protons, isotopically pure phosphate compounds substantially free of deuterium, isotopically pure phosphate compounds substantially free of protons, or mixtures thereof to the human to thereby effect the mental change in the human. In particular, wherein the human has an affective disorder.

Further still, the present invention provides a method for chemically changing a biological clock of a human which comprises administering an effective amount of isotopically pure heavy water substantially free of protons, isotopically pure hydrogen-containing water substantially free of deuterium, isotopically pure carbonate compounds substantially free of deuterium, isotopically pure carbonate compounds substantially free of protons, isotopically pure phosphate compounds substantially free of deuterium, isotopically pure phosphate compounds substantially free of protons, or mixtures thereof, to the patient so that the biological clock is changed. This method is particularly useful when the patient has a bipolar disorder.

Isotopically pure heavy water substantially free of protons, isotopically pure hydrogen-containing water substantially free of deuterium, isotopically pure carbonate compounds substantially free of deuterium, isotopically pure carbonate compounds substantially free of protons, isotopically pure phosphate compounds substantially free of deuterium, isotopically pure phosphate compounds substantially free of protons, or mixtures thereof are claimed and methods for preparing the isotopically pure compounds are provided.

Therefore, it is an objective of the present invention to provide isotopically pure heavy water substantially free of protons, isotopically pure hydrogen-containing water substantially free of deuterium, isotopically pure carbonate compounds substantially free of deuterium, isotopically pure carbonate compounds substantially free of protons, isotopically pure phosphate compounds substantially free of deuterium, isotopically pure phosphate compounds substantially free of protons, or mixtures thereof for the treatment of psychiatric disorders in a patient by administering the heavy water or deuterated carbonate compound to the patient.

It is also an object of the present invention to provide a compound for the treatment of psychiatric disorders such as bipolar disorders that is safer than the compounds which are currently used for treating psychiatric disorders.

DESCRIPTION OF PREFERRED EMBODIMENTS

All patents, patent applications, government publications, government regulations, and literature references cited in this specification are hereby incorporated herein by reference in their entirety. In case of conflict, the present description, including definitions, will control.

As used herein, the term "proton" refers to "hydrogen atom," "hydrogen ion," "hydrogen moiety," or "protium atom" and is used herein to mean hydrogen atom or protium atom.

As used herein, the term "deuteron" refers to "deuterium," "deuterium ion," "deuterium moiety," or "deuterium atom" and is used herein to mean deuterium atom.

As used herein, the term "isotopically pure" means a molecule, compound, or reagent wherein substantially all protons (ions or nuclei) contained therein are replaced with deuterons or wherein substantially all the deuterons are replaced with protons. The isotopically pure molecules can be made either chemically in reactions using isotopically pure water or biologically by growing organisms such as bacteria in a isotopically pure medium or plants wherein the water source is isotopically pure hydrogen-containing water or heavy water. Such "isotopically pure" compounds can contain tritium but not at levels which are physiologically harmful or above the naturally occurring background level found in potable water.

As used herein, the term "substantially free of protons or deuterons" means for pharmacological purposes, since it is impossible to remove all protons or deuterons from a compound.

As used herein, the term "isotopically pure compound" means a compound consisting of the isotopically pure molecules to within physiologically active amounts of any adulterant isotope. For example, as used herein, the term "isotopically pure hydrogen-containing carbonate" means carbonate that is substantially free of deuterium and the term "isotopically pure deutrocarbonate" or "deuterated carbonate" means carbonate that is substantially free of protons within the above physiological limits. Preferably, when the carbonate compound is in a non-psychoactive pharmaceutical carrier, the carrier is also isotopically pure. However, it must be kept in mind that natural, normally consumable water contains about 0.5% $D_2O$.

The term "therapeutically effective amount" means those amounts of the isotopically pure molecules in an isotopically pure compound, which have been determined to provide the desired psychiatric effect without side effects that are considered clinically unacceptable.

As used herein, the term "deuterated carbonate" refers to either sodium bideuterocarbonate, which has the formula $DNaCO_3$.

As used herein, the term "substantially free" means less than 0.001 mole percent of deuterium in molecules substantially free of deuterium and less than 0.001 mole-percent of protons in molecules substantially free of protons.

Deuterium, or heavy hydrogen, is a stable, non-radioactive isotope of hydrogen and has an atomic weight of 2.0144. It is represented by the symbol D or $^2H$ and usually exists in the diatomic state but may exist in a monoatomic state. For example, sea water has been shown to contain HDO. In nature it is a colorless and odorless gas, liquid, or solid. It is well known in the art that in the natural world, hydrogen actually represents a mixture of the isotopes $^1H$ (hydrogen or proton), D ($^2H$ or deuterium), and T ($^3H$ or tritium). Thus, in nature all chemical molecules comprising hydrogen (or protium) atoms or protons are always present in a mixture of molecules containing protium atoms, deuterium atoms, and tritium atoms. In general, the portion of deuterium amounts to about 1.5 mole-percent.

Manic depression or bipolar disorder is a neurological brain disorder involving extreme swings in mood, i.e., recycling between periods of mania and periods of depression. Manic depression is one of four mood disorders, the others being unipolar depressive disorder (depression only), unipolar (mania only), and schizoaffective disorder (See Manual IV, American Psychiatric Association). Patients suffering from mania generally have a shortened circadian rhythm and patients suffering from depression generally have a lengthened circadian rhythm.

Currently, treating bipolar and unipolar disorders consists of a combination of psychotherapy, teaching learning life-adjustment skills, and using mood stabilizers such as lithium (LITHOBID), and valproic acid (sold as DEPAKOTE or VALPROMEX by Abbott Laboratories, Illinois). The goal of the treatment is to effect a mental change in the person suffering from the disorder from a mental state characterized by mood swings to a stabilized mental state no longer afflicted by mood swings between mania and depression nor by prolonged bursts of manic agitation, nor depressive dispondancy. For example, treating the patient with bipolar disorder with a compound that prevents or reduces the manic period, the biphasic cycle between mania and depression is broken and the patient is stabilized in mental state that is not subject to mood swings.

The most common treatment of bipolar disorders is administering lithium to the patient. The effects of lithium may take up to 2 weeks to take affect, but in general, up to 80% of patients with bipolar disorder who are prescribed lithium receive beneficial effects from it. Lithium tends to prevent the recurrence of additional depressive or manic episodes, if medication compliance is maintained by the patient.

For those patients who cannot tolerate lithium carbonate or its side effects, though, there are few treatment options for mania. DEPAKOTE is the most commonly prescribed treatment alternative to lithium, but frequently causes blood dyscrasias. Anti-psychotic medication is prescribed in more rare instances, such as haloperidol or chlorpromazine. The prognosis for such patients is markedly poorer than that of patients who can tolerate lithium or valproic acid. There is considerable doubt about the efficaciousness of valproic acid in the present literature. The reason for this differentiation is unclear. Anti-psychotic medications also tend to interfere more with normal cognitive functioning and have notably increased side-effects. They are generally tolerated less well than lithium because of their side effects; and medication compliance is usually, therefore, an equally important issue. However, lithium and valproic acid generally have little effect on a major depressive episode; these episodes should first be treated by an appropriate antidepressant medication.

The circadian rhythm or biological clock is fundamental to all organisms and has a profound role in all aspects of the physiology of the organism. It may also have an important effect on the cycle between mania and depression in patients with bipolar disorders. A number of chemicals have been found to increase the length of the biological clock. For example, heavy water ($D_2O$), lithium salts, ethanol, and the antibiotic valinomycin have been shown to lengthen the biological clock (Saunders in *An Introduction to Biological Rhythms*. Blackie & Son Ltd., Glasgow, Scotland. 1977. pp. 142–155). Experiments with deer mice showed that the effect of $D_2O$ on the biological clock was dose dependent and reversible (Saunders, ibid.). That is, it was found that as the ratio of $D_2O$ to $H_2O$ was increased in the drinking water that was supplied to the deer mice, there was a corresponding increase in the endogenous daily cycle of the mice.

It is believed that deuterons ($D^+$) and lithium ions influence ionic balances across cellular membranes albeit by different mechanisms. $D^+$ has a heavier mass than $H^+$ and it is believed that the increased mass slows diffusion across the membrane. In contrast, lithium ions (and ethanol and valinomycin) are believed to exert their effect by affecting membrane permeability. Therefore, because deuterium ions and lithium ions affect the length of the period of the biological clock (or alternatively, lengthen the cycle of the biological rhythm), it is believed that ions and membrane permeability are involved in the circadian rhythm, if not a part of the clockwork itself. A model has been proposed by Njus et al. (Nature, London. 248: 116–120 (1974)) for circadian rhythmicity that is based on a feedback mechanism between ion concentrations and the activities of membrane-bound ion transport systems. "[L]ight is presumed to act by perturbing ion concentrations, probably K+, which pass through photosensitive ion gates to augment or deplete the K+ concentration directly. In higher systems, hormones could mediate between specialized photoreceptors and the membrane. Since the clock is envisaged as a feedback between ions and membranes, there must be circadian changes in transmembrane ion fluxes, probably involving the activation and inhibition of transport proteins in the membrane." (Saunders, ibid., at 150).

The ratio of deuterium to protium atoms in a compound appears to clearly have an affect on the circadian rhythm in humans. The average circadian rhythm in humans is a day cycle of about 24.5 hours with sleep constituting about eight hours of the day cycle. In manics the day cycle is shorter and is on average about 23 hours. In depressives the day cycle is longer and is on average about 25 hours. Compounds with a higher than normal ratio or mole-percent of deuterium atoms increase the day cycle whereas the compounds with a lower than normal ratio or mole-percent of deuterium atoms decrease the day cycle. Therefore, administering deuterated compounds to a patient suffering from mania increases the day cycle of the patient, which can provide relief to a patient suffering from the effects of the mania. Conversely, administering substantially deuterium-free compounds to a patient suffering from depression can shorten the day cycle, which can provide relief to the patient from the effects of the depression.

The present invention provides the following preferred compounds: compounds consisting of isotopically pure heavy water substantially free of protons, isotopically pure hydrogen-containing water substantially free of deuterium, isotopically pure carbonate molecules substantially free of deuterium (e.g., $H_2CO_3$ or $NaHCO_3$), isotopically pure compounds consisting of isotopically pure deuterated carbonate molecules substantially free of protons (e.g., $D_2CO_3$ or $NaDCO_3$), isotopically pure phosphate molecules substantially free of deuterium (e.g., $H_2PO_4$ or $CaHPO_4$), isotopically pure compounds consisting of isotopically pure deuterated phosphate molecules substantially free of protons (e.g., $CaDPO_4$), and mixtures thereof. The present invention further provides isotopically pure compositions and mixtures comprising the above molecules, containing a ratio or mole-percent of deuterium to protons that is greater or lesser than the naturally occurring ratio or mole-percent in an isotopically pure deuterated carrier molecule or substance that is substantially free of protons, an isotopically pure carrier substantially free of deuterium, a carrier that has a ratio or mole-percent of deuterium to protons that is greater or lesser than the naturally occurring ratio or mole-percent, or mixtures thereof.

The present invention also provides a method for using compounds that consist of isotopically pure heavy water substantially free of protons, isotopically pure hydrogen-containing water substantially free of deuterium, isotopically pure phosphate or carbonate compounds substantially free of deuterium (e.g., $CaHPO_4$ (calcium hydrogen phosphate) or $NaHCO_3$), isotopically pure deuterated phosphate or carbonate compounds substantially free of protons (e.g., $CaDPO_4$ (calcium deuteron phosphate) or $NaDCO_3$), or mixtures thereof for treating various psychiatric disorders, such as treating the depression phase in patients with bipolar disorders, treating mania in patients with bipolar disorders, and treating depression in patients with unipolar disorders.

Thus, the present invention provides a method of treating a depressive symptom in a human patient, which comprises administering to the patient in a therapeutically effective amount of isotopically pure hydrogen-containing water substantially free of deuterium, isotopically pure phosphate or carbonate compounds substantially free of deuterium (e.g., $CaHPO_4$ or $NaHCO_3$), or mixtures thereof, which reduces the depressive symptoms of the patient by reducing the day cycle of the patient to a day cycle of about 24.5 hours, which is the day cycle of normal humans. Preferably, the compound is absorbed by the pineal gland, the superchiasmatic nucleus (SCN), or both. In particular embodiments, the above compounds can contain particular ratios of isotopically pure heavy water substantially free of protons, isotopically pure hydrogen-containing water substantially free of deuterium, isotopically pure carbonate compounds substantially free of deuterium (e.g., $H_2CO_3$ or $NaHCO_3$), and isotopically pure phosphate or carbonate compounds substantially free of protons (e.g., $CaDPO_4$ or $NaDCO_3$).

The present invention further provides a method of treating a manic symptom in a human patient, which comprises administering to the patient in a therapeutically effective amount a compound consisting of isotopically pure heavy water substantially free of protons, isotopically pure deuterated carbonate compounds substantially free of protons (e.g., $NaDCO_3$), or mixtures thereof, which reduces the manic symptoms of the patient by increasing the day cycle of the patient to a day cycle of about 24.5 hours, which is the day cycle of normal humans. Preferably, the compound is absorbed by the pineal gland, the superchiasmatic nucleus (SCN), or both. In particular embodiments, the above compounds can include particular ratios of isotopically pure heavy water substantially free of protons, isotopically pure hydrogen-containing water substantially free of deuterium, isotopically pure phosphate or carbonate compounds substantially free of deuterium (e.g., $CaHPO_4$ or $NaHCO_3$), and isotopically pure phosphate or carbonate compounds substantially free of protons (e.g., $CaDPO_4$ or $NaDCO_3$).

The treatment of mania or depression is effected by using compositions with particular ratios of isotopically pure deuterated carbonate substantially free of protons to isotopically pure hydrogen containing carbonate substantially free of deuterium. For example, compositions with a ratio or mole-percent of deuterium to protons that is less than the naturally occurring ratio or mole-percent would decrease the day cycle of a patient with a depressive symptom whereas compositions with a ratio or mole-percent of deuterium to protons greater than the naturally occurring ratio or mole-percent would increase the day cycle of a patient with a manic symptom.

Therefore, the phosphate, carbonate, or both compounds of the present invention are administered to a patient in a treatment regimen to (1) increase activity of the patient, (2) decrease activity of the patient, (3) enhance normal sleep patterns in the patient, (4) accelerate the patient's circadian rhythms, or (5) decrease the amplitude of activity variation in the patient's circadian rhythms. The compounds can be dispensed in liquid, capsule, or tabular form in dosages that are pharmacologically efficacious. Alternatively, the compounds can be administered to a patient intravenously.

Thus, the present invention provides a method for chemically changing a biological clock of a human, which comprises administering an effective amount of isotopically pure heavy water substantially free of protons, isotopically pure hydrogen-containing water substantially free of deuterium, isotopically pure phosphate or carbonate compounds substantially free of deuterium (e.g., $CaHPO_4$, $H_2CO_3$ or $NaHCO_3$), isotopically pure phosphate or carbonate compounds substantially free of protons (e.g., $CaDPO_4$, $D_2CO_3$ or $NaDCO_3$), or mixtures thereof to the patient so that the biological clock is changed. The effective amounts of the waters are can further include in any ratio of $H_2O$, $D_2O$, and HDO. $CaHPO_4$, $CaDPO_4$, $NaHCO_3$, and $NaDCO_3$ are hydroscopic salts which are preferably encapsulated.

The above compositions containing deuterated carbonate can further include lithium carbonate. It is believed that for treating particular cases of mania it is desirable to provide compositions that contain particular ratios of isotopically pure deuterated carbonate or heavy water and lithium carbonate. Because of the different mechanisms by which the deuterated carbonate or heavy water and the lithium carbonate effect a lengthening of the day cycle, the combination of deuterated carbonate or heavy water and lithium carbonate act synergistically to reduce the occurrence, severity, and duration of mania in a patient with a bipolar disorder.

Thus, the present invention provides a plurality of compounds or mixtures containing particular ratios or mole-percent of isotopically pure heavy water and/or deuterated phosphate or bicarbonate and isotopically pure hydrogen-containing water and/or nondeuterated phosphate or carbonate, which are useful for treating a wide range of psychiatric disorders that are either caused by chronoregulation disorders or that can be controlled by altering the biological activity of the biological clock. This can be effected by equilibrium deuteration wherein a particular level of deuterium is maintained in the pineal gland, which is accomplished by providing a sufficient amount of particular ratios of the deuterated or hydrogen-containing compounds or waters to the patient for a therapeutically effective period of time.

As has been shown herein, it is claimed that the chemical compounds herein described serve the purpose of transporting, differentially, protons or deuterons, to or away from the region of the synchronizing chemical clock in the region of the pineal gland in the human brain thus adjusting its periodic cycle, and thereby favorably affecting mood or sleep processes.

The isotopically pure heavy water substantially free of protons, isotopically pure hydrogen-containing water substantially free of deuterium, isotopically pure phosphate or carbonate compounds substantially free of deuterium (e.g., $CaHPO_4$, $H_2CO_3$ or $NaHCO_3$), isotopically pure phosphate or carbonate compounds substantially free of protons (e.g., $CaDPO_4$, $D_2CO_3$ or $NaDCO_3$) compounds of the present invention are prepared by chemical reactions in isotopically pure water and ion exchange methods, which exchange protons for deuterium and tritium atoms.

A preferred isotopically pure reagent for making protium- and tritium-free therapeutic compounds of the present invention is isotopically pure heavy water. Isotopically pure heavy water is used to make deuterated carbonate wherein the proton in the O—H bond is exchanged for deuterium in a chemical exchange reaction. Generally, the compound is dissolved in isotopically pure heavy water and the solution is maintained at a temperature between room temperature and boiling temperature of the isotopically pure heavy water for a sufficient period of time with suitable catalysts or ion exchange media. Afterwards, the solution is allowed to cool and the deuterated carbonate is crystallized from the isotopically pure heavy water or is removed from the isotopically pure heavy water by evaporation under a vacuum. The above exchange reaction is particularly efficient in exchanging deuterium for protons in the readily exchangeable O—H bonds. Infrared photocatalysis spectra can be used to increase the efficiency of the reaction. This method is based upon the method disclosed in U.S. Pat. No. 5,895,660 to Hoffman et al., which is hereby incorporated herein by reference. Laser irradiation can be used to enhance the efficiency of the reaction.

Incorporating sources of electromagnetic radiation such as microwave tubes or tunable lasers, photocatalysis is used to selectively break C—R, N—R, and O—R bonds where R is a protium, thus allowing replacement with a deuterium atom. By illuminating an ion-exchange medium, previously charged with deuterium atoms, with proper wavelengths of optical energy, the exchange of protium and tritium atoms for the deuterium atoms can be facilitated. Deposition of the ion-exchange medium in a thin layer can make this process more effective by allowing all of the substrate to be illuminated.

Alternatively, the deuterated carbonate compound is made by column chromatography, which exchanges the protium and tritium atoms in bond with oxygen with deuterium atoms. The method involves (a) providing a deuterium loaded ion exchange column; (b) introducing the hydrogenated compound onto the column so that protium in bond with the oxygen are replaced with deuterium atoms; and (c) removing the deuterated compound from the column. in one embodiment, the column is packed with a polystyrene sulfate sodium ion exchange resin such as polystyrene sulfate-sodium or equivalent ion exchange resin. Next, the column is prepared by washing the column with isotopically pure deuterochloric acid. Then, the carbonate is passed through the column wherein the protium atoms in the compound are exchanged with the deuterium atoms in the column. The deuterated carbonate is then eluted from the column.

The above method can be used to make isotopically pure carbonate compounds by substituting the heavy water or deuterated chloric acid with isotopically pure water or isotopically pure hydrochloric acid.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A method of treating a depressive symptom in a human patient which comprises administering an isotopically pure deuterated carbonate compound, substantially free of protons, to the patient in an amount which reduces the depressive symptom of the patient.

2. The method of claim 1 wherein the patient has a bipolar disorder.

3. The method of claim 1 wherein the compound is selected from the group consisting of bideuterocarbonate and deuterocarbonate.

4. A method of treating a manic symptom in a human patient with a bipolar disorder which comprises administering an isotopically pure deuterated carbonate compound, substantially free of protons, to the patient in an amount which reduces the manic symptom of the patient.

5. The method of claim 4 wherein the compound is selected from the group consisting of bideuterocarbonate and deuterocarbonate.

6. A method for effecting an improved mental condition in a human affected with a mental disorder which comprises administering an effective amount of an isotopically pure deuterated carbonate compound, substantially free of protons, to thereby effect the improved mental condition in the human patient.

7. The method of claim 6 wherein the patient has a bipolar disorder.

8. The method of claim 6 wherein the compound is selected from the group consisting of bideuterocarbonate and deuterocarbonate.

* * * * *